(12) United States Patent
Derzon et al.

(10) Patent No.: US 9,681,846 B1
(45) Date of Patent: Jun. 20, 2017

(54) CATHETERIZED PLASMA X-RAY SOURCE

(71) Applicant: Sandia Corporation, Albuquerque, NM (US)

(72) Inventors: Mark S. Derzon, Albuquerque, NM (US); Alex Robinson, Albuquerque, NM (US); Paul C. Galambos, Albuquerque, NM (US)

(73) Assignee: National Technology & Engineering Solutions of Sandia, LLC, Albuquerque, NM (US)

( * ) Notice: Subject to any disclaimer, the term of this patent is extended or adjusted under 35 U.S.C. 154(b) by 786 days.

(21) Appl. No.: 14/102,422

(22) Filed: Dec. 10, 2013

(51) Int. Cl.
*A61N 5/10* (2006.01)
*H05G 2/00* (2006.01)
*A61B 6/00* (2006.01)
*H01J 35/02* (2006.01)

(52) U.S. Cl.
CPC .......... *A61B 6/4057* (2013.01); *A61N 5/1014* (2013.01); *H01J 35/02* (2013.01); *H05G 2/003* (2013.01); *H05G 2/006* (2013.01)

(58) Field of Classification Search
CPC .... A61N 5/1001; A61N 5/1019; H05G 2/001; H05G 2/003; H05G 2/006
See application file for complete search history.

(56) References Cited

U.S. PATENT DOCUMENTS

| | | | |
|---|---|---|---|
| 5,525,805 A | 6/1996 | Greenly | |
| 6,324,257 B1 * | 11/2001 | Halavee | A61N 5/1001 378/121 |
| 6,438,206 B1 * | 8/2002 | Shinar | A61N 5/1001 378/119 |
| 6,586,757 B2 | 7/2003 | Melnychuk et al. | |
| 7,291,853 B2 | 11/2007 | Fomenkov et al. | |
| 8,530,854 B1 | 9/2013 | Derzon et al. | |
| 2004/0208285 A1 * | 10/2004 | Freudenberger | A61N 5/1001 378/119 |
| 2004/0218721 A1 * | 11/2004 | Chornenky | A61N 5/1015 378/119 |
| 2012/0080618 A1 * | 4/2012 | Clayton | H05H 15/00 250/492.3 |

OTHER PUBLICATIONS

Chittenden, et al., "Structural Evolution and Formation of High-Pressure Plasmas in X Pinches," Phys Rev Lett 98, 025003 (2007).
Galmabos et al., "Active MEMS Valves for Flow Control in a High Pressure Micro-Gas-Analyzer", J Microelectromech Sys, 20(5) (2011).

(Continued)

*Primary Examiner* — Glen Kao
(74) *Attorney, Agent, or Firm* — Martin I. Finston (57) ABSTRACT

A radiation generator useful for medical applications, among others, is provided. The radiation generator includes a catheter; a plasma discharge chamber situated within a terminal portion of the catheter, a cathode and an anode positioned within the plasma discharge chamber and separated by a gap, and a high-voltage transmission line extensive through the interior of the catheter and terminating on the cathode and anode so as to deliver, in operation, one or more voltage pulses across the gap.

6 Claims, 7 Drawing Sheets

(56) References Cited

OTHER PUBLICATIONS

Galambos et al., "Passive MEMS Valves With Preset Operating Pressures for Microgas Analyzer", J Microelectromech Sys, 18(1) (2009).
Derzon et al., "Analytical estimation of neutron yield in micro gas-puff x pinch," J App Phys 112, 114516 (2012).
Krishnan, et al., "A Fast Pulsed Neutron Source for Time-of-Flight Detection of Nuclear Materials and Explosives," AIP Conf. Proc. 1412, Crete, Greece (2011).
Lacoste, et al., "Breakdown characteristics of a nanosecond-pulsed plasma discharge in supercritical air," Plasma Sources Sci Technol 21 (2012).
Louisos, et al., "Design considerations for supersonic micronozzels", Int J Manufacturing Research, pp. 1-31, A Chapter of the Encyclopedia of Microfluidics and NanoFluidics, Springer Publishers, 2008.
Papadopoulos, et al., "Air Entrainment Studies for a Supersonic Micro-Ejector System," Proceedings of FEDSM2008, 2008 ASME Fluids Engineering Conference, Jacksonville, Florida USA (2008).
Santoni, F. et al., "Micropropulsion Experiment on UNISAT-2", Aerospace Conference Proceedings, IEEE, vol. 1, pp. 1-479-1-486 (2002).
Shelkovenko, et al., "X Pinch Plasma Development as a Function of Wire Material and Current Pulse Parameters," Plasma Science, IEEE Transactions 30(2) pp. 567-576 (2002).
Soto, et al., "Nanofocus: an ultra-miniature dense pinch plasma focus device with submillimetric anode operating at 01 J", Plasma Sources Sci Technol, 18 (2009).
Soukhanovskii, V.A., "Supersonic gas injector for fueling and diagnostic applications on the National Spherical Torus Experiment", Rev. Sci. Instrum. 75, 4320, pp. 4320-4323 (2004).

\* cited by examiner

CATHETERIZED PLASMA X-RAY SOURCE

STATEMENT OF GOVERNMENTAL INTEREST

This invention was developed under contract DE-AC04-94AL85000 between Sandia Corporation and the U.S. Department of Energy. The U.S. Government has certain rights in this invention.

BACKGROUND

Heated plasmas are known to be useful for the generation of x-radiation and for the generation of neutrons through the nuclear fusion of light ions, typically hydrogen and its isotopes. There has been a great deal of recent interest in z-pinch and x-pinch techniques, in which a plasma is compressed under the influence of its own magnetic field, which leads to both temporary confinement and adiabatic heating of the plasma.

In particular, so-called "micropinch" techniques have been developed, in which a small puff of gas (i.e., a "micropuff") is ionized and electromagnetically excited by a high-voltage pulse, typically of on the order of kilovolts in amplitude and microseconds in duration. The puff of gas is emitted from a nozzle that may be configured for subsonic, sonic, or supersonic gas emission. For example, nozzles of the converging-diverging, or Laval, design, among others, have been found useful for generating gas puffs at Mach numbers up to M=8 or more, while also being amenable to miniaturization.

For example, U.S. Pat. No. 8,530,854, which is commonly owned herewith, issued on Sep. 10, 2013 to M. S. Derzon et al. under the title "Micro Gas-Puff Based Source." That patent discloses several approaches to the design of a plasma source that uses a micro-scale gas puff to generate neutrons, x-radiation, or other energetic particles. The source as described there has a diode configuration including an anode and a cathode and a reaction chamber included between them. A micro-electromechanical systems (MEMS) gas supply injects a puff of gas between the anode and the cathode within the chamber. A pulsed power supply applies the voltage between the electrodes that compresses the gas puff to form the plasma. In some embodiments, the gas supply is adapted to create a quasispherical gas density profile, i.e. a profile that is cylindrically symmetrical but dependent on the azimuthal coordinate in such a way that when the power supply discharges, the puff will implode under its own magnetic field in a manner that tends to concentrate the heating effect near its center. The entirety of U.S. Pat. No. 8,530,854 is hereby incorporated herein by reference.

In the field of medical imaging, it has long been conventional to generate x-rays by the beam-on-target technique. That technique is well-established, not least because of extensive history, low cost over the equipment lifetime, the reusability of targets, and the well-known characteristics of the x-ray line radiation that is produced.

Plasma generation of x-rays, by contrast, has not found general acceptance for medical imaging or for other radiological techniques such as the treatment of tumors. This is partly because it is relatively new, but also because equipment is generally expensive, discharge chambers have short lifetimes, and the predominant x-radiation that is produced is not line radiation. However, if plasma x-ray sources could be made more acceptable, they would offer advantages, potentially including greater spatial resolution and lower overall radiation dose, that would give them a role for at least some important applications in radiological medicine.

In the field of radiological treatment of tumors, it has been conventional to use x-rays generated by beam-on-target devices or radiation from radioisotopes. Radioisotope use is also well-established, not least because of extensive history and relatively low cost. However, radiological treatment as currently administered often results in unnecessarily high doses of radiation to the patient.

Thus, there remains a need for adaptations that can make plasma x-ray sources, and possibly other radiation sources, practical as an alternative radiation source for medical and other applications.

SUMMARY

We have made such an adaptation. Our adaptation is to enclose the cathode, anode, and reaction chamber of a pinched plasma radiation source at the end of a catheter that is used to deliver a localized radiation dose within the body of a living subject. A narrow transmission line that fits within the catheter is used to transmit an electrical pulse to a small-pinch plasma load. For example, a transmission line less than 3 mm in diameter can be used to transmit a pulse up to 100 kilovolts, of pulse width up to 50 ns, and of total energy up to 1 J, to deliver a dose of x-rays predominantly in the range 10-60 keV. Our calculations predict that local doses at least in the range 100 to 1000 rad will be available with this technique.

It has been reported that there are 20,000 excess deaths each in year in the US alone from excess radiation exposure. Thus there is a great need for more efficient radiation delivery techniques that reduce the overall exposure suffered by patients. We believe that our technique for delivering a localized radiation dose from the end of a catheter can substantially reduce the dose delivered to the patient, relative to conventional isotopic and other sources.

In various implementations, particularly for use as a bright x-ray source for cancer treatment and the like, the plasma diode can be configured for small dense plasma-focus operation or for z-pinch operation, among others.

In other implementations, particularly for imaging applications, non-thermal features of the plasma can be used to enhance inner-shell x-ray production and tune the line energy of the excited gas, such as xenon or krypton.

Known microfabrication techniques, particularly silicon MEMS techniques, can be used to make nozzles and valves on dimensional scales pertinent to the micropinch plasmas.

Accordingly, our invention in one aspect relates to a radiation-generating apparatus that includes a catheter, a plasma discharge chamber situated within a terminal portion of the catheter, a cathode and an anode positioned within the plasma discharge chamber and separated by a gap, and a high-voltage transmission line extensive through the interior of the catheter and terminating on the cathode and anode. The transmission line is arranged so that in operation, it will deliver one or more voltage pulses across the gap.

In another aspect, our invention relates to a method for irradiating a subject, including steps of positioning a catheter within the subject, and exciting a plasma discharge in a chamber situated within the catheter such that radiation is emitted from the chamber. In embodiments, a plasma-forming fluid is flowed into the catheter, and a puff of the fluid is injected into the plasma discharge chamber prior to exciting the plasma discharge. In embodiments, the plasma discharge is excited so as to generate a non-equilibrium plasma that emits more x-radiation at photon energies above 10 keV than a comparable equilibrium plasma.

In embodiments, the subject is a living subject, and the method is performed so as to irradiate a tumor in the living subject.

In embodiments, the subject is a living subject, the emitted radiation is x-radiation, and the method further comprises intercepting a portion of the x-radiation at an imaging detector or imaging detector array after it has passed through tissue belonging to the living subject.

DETAILED DESCRIPTION

As described, e.g., in the above-cited U.S. Pat. No. 8,530,854 and depicted in FIG. 1, an exemplary micropuff source 100 includes a diode 102 that in turn includes an anode 104, a cathode 106, and a reaction chamber 108 situated between the anode 104 and the cathode 106. In implementations, chamber 108 is evacuated to low pressure, e.g. to a pressure less than 10 Torr.

Figure 1:
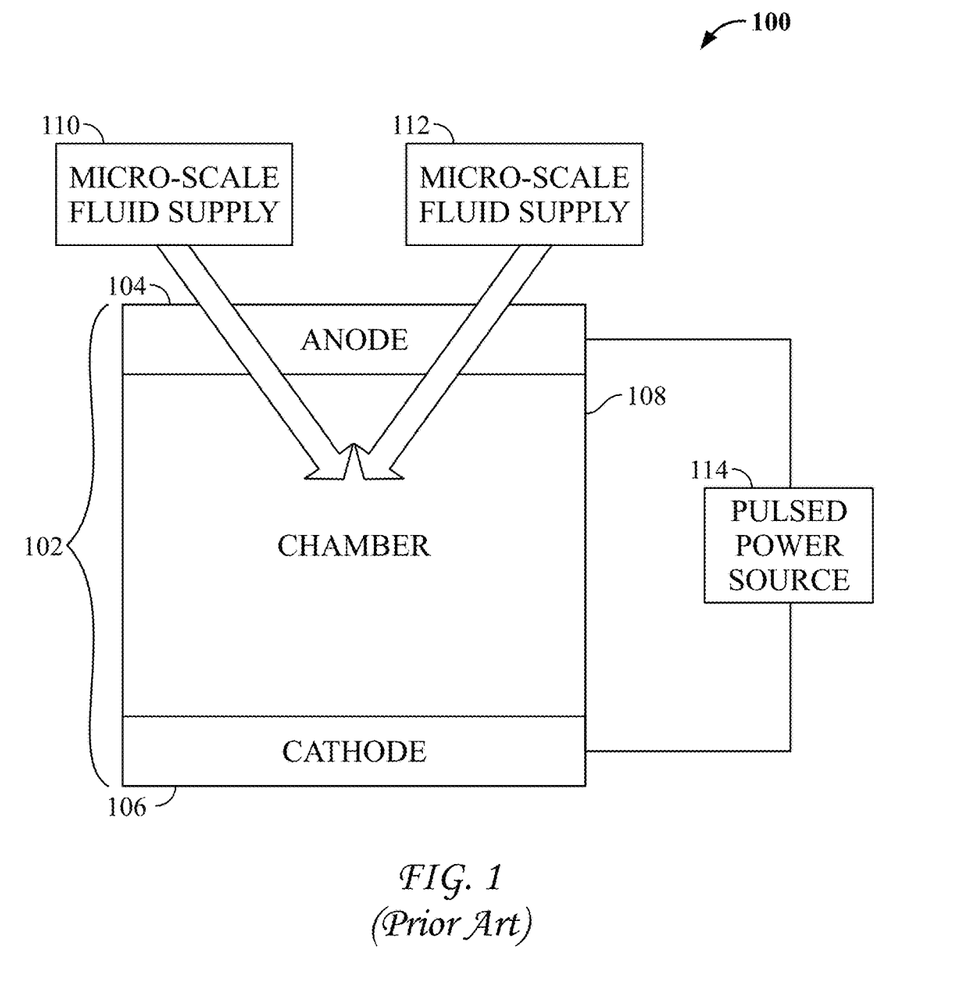
FIG. 1 illustrates a block diagram of an exemplary micro fluid-puff based source of neutrons, x-rays, or energetic particles as known in the prior art.

Source 100 further includes a micro-scale gas supply 110 adapted to inject a jet of gas, i.e. the gas "puff", between the anode 104 and the cathode 106 within the chamber 108. In at least some implementations, the micro-scale gas supply 110 is further adapted to shape the gas puff to form a quasispherical density profile. For example, x-pinches are generally quasispherical in nature. The symmetry of typical z-pinches is generally more cylindrical than spherical in nature, but as z-pinch configurations are made shorter they may approach quasispherical behavior. Dense plasma focus configurations can dynamically approach quasispherical behavior.

In some implementations, the micro-scale gas supply 110 may be embedded in the anode 104. In other implementations, the micro-scale gas supply 110 may be embedded in the cathode 106. In fact, one electrode may be made coextensive with the nozzle. The choice of which polarity (relative to the direction of the gas jet) to use may depend, at least in part, on what are expected to be the most damaging accelerated particles in a given application. That is, if a high, energetic flux of electrons is expected, it is advantageous to accelerate the electrons from the nozzle toward an opposing electrode having a perforation through which the electrons can proceed toward a stop plate. On the other hand, if a high, energetic flux of positive ions is expected, it is advantageous to use a similar configuration, but with the opposite polarity.

It should be noted in this regard that although the micropuff is referred to throughout this discussion as constituted by a gas, the invention is by no means so limited. Instead, the substance that forms the micropuff should more generally be regarded as a fluid that may be either liquid or gas. In fact, it may even be the case that cooling due to adiabatic expansion of, e.g., a liquified gas as it emerges from the nozzle may solidify it, so that the micropuff is initially constituted by a suspension of solid particles.

The micro-scale gas supply 110 includes a nozzle and a valve formed, e.g., by MEMS techniques. As depicted in FIG. 1, the micro-scale gas supply is configured to provide two intersecting jets of gas, so as to form a plasma with an x-pinch configuration as known in the art. It should be noted that configurations using a single jet, so as to form for example a plasma with a z-pinch or dense plasma focus configuration as also known in the art, are not excluded from the scope of the present invention and may in fact be preferred for at least some implementations.

A pulsed power source 114 is coupled to the anode and cathode to apply the voltage discharge that causes compression of the gas puff and thereby generate the plasma. One example of a pulsed power source useful in this regard is a Marx generator. Another example is a linear transformer driver (LTD).

Figure 2:
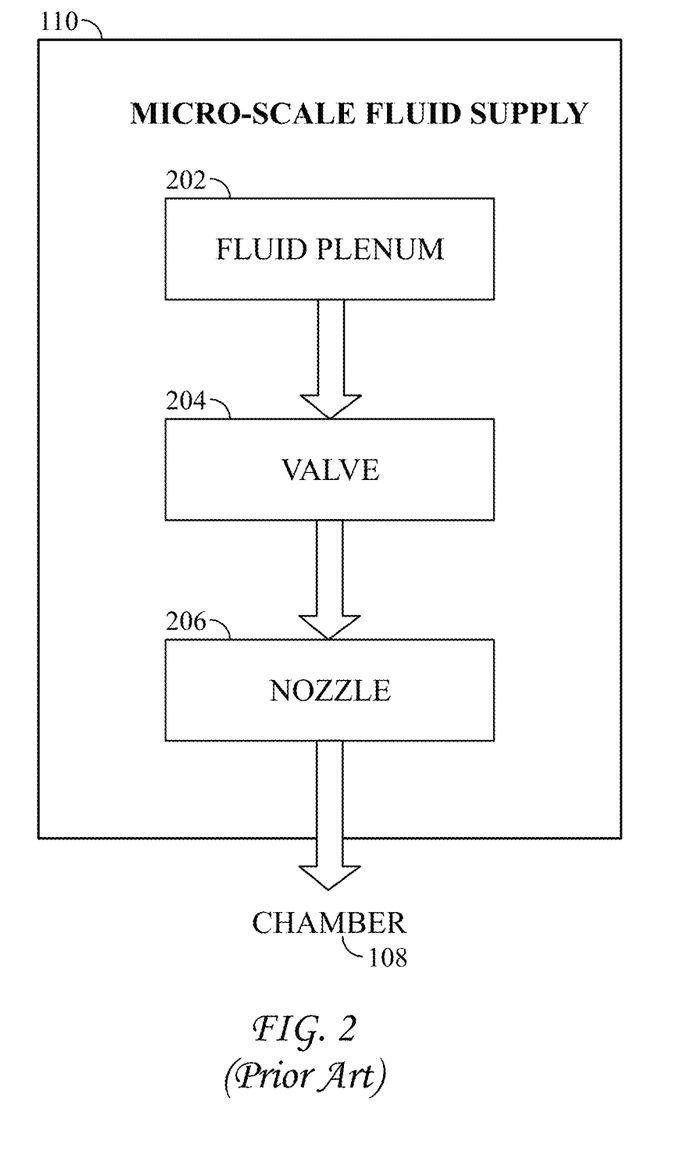
FIG. 2 illustrates a block diagram of an exemplary micro-scale fluid supply included in the micro fluid-puff based source of FIG. 1.

With reference to FIG. 2, the micro-scale gas supply 110 includes a gas plenum 202, a valve 204 coupled to the plenum, and a nozzle 206 coupled to the valve. The opening of valve 204 admits gas from plenum 202 through valve 204 and nozzle 206 into chamber 108.

Micro-scale gas supplies and their components, as well as micro-scale plasma pinch devices, are known. For example, G. Papadopoulos et al., "Air Entrainment Studies for a Supersonic Micro-Ejector System," *Proc. FEDSM2008 ASME Fluids Eng. Conf.* (Aug. 10-14, 2008), Jacksonville, Fla., FEDSM2008-55220, pp. 1-7 describes a supersonic nozzle made using silicon microfabrication techniques. F. Santoni et al., "Micropropulsion Experiment on UNISAT-2," 2002 *IEEE Aerospace Conference Proc.* (2002), Vols. 1-7, pp. 1-479 to 1-486, describes a submillimeter microthruster nozzle manufactured on a silicon chip. M. Krishnan et al., "A Fast Pulsed Neutron Source for Time-of-Flight Detection of Nuclear Materials and Explosives," *Applications of Nuclear Techniques: Eleventh Int. Conf.*, M. E. Hamm and R. W. Hamm, eds., Vol. 1412 (2011), pp. 1-4, describes a dense plasma focus (DPF) device constructed on a spatial scale of tens of millimeters. L. Soto et al., "Nanofocus: an ultra-miniature dense pinch plasma focus device with submillimetric anode operating at 0.1 J," *Plasma Sources Sci. Technol.* 18 (2009) 015007 (5 pp.), describes a pinch plasma focus device constructed on a millimeter spatial scale. M. S. Derzon et al., "Analytical estimation of neutron yield in a micro gas-puff X pinch," *J. Appl. Phys.* 112, 114516 (2012) (14 pp.), provides a conceptual design of a micro-scale x-pinch device and includes a review of pertinent nozzle technology. P. Galambos et al., "Passive MEMS Valves With Preset Operating Pressures for Micro-gas Analyzer," J. Microelectromechanical Syst. 18 (February 2009) 14-27, describes a valve made using silicon microfabrication techniques. P. Galambos et al., "Active MEMS Valves for Flow Control in a High-Pressure Micro- Gas-Analyzer," J. Microelectromechanical Syst. 20 (October 2011) 1150-1162, also describes a valve made using silicon microfabrication techniques. All of the publications listed above are hereby incorporated herein by reference.

Those skilled in the art will understand that design details of plenum 202, valve 204, nozzle 206, and chamber 108, as well as the input gas pressure and the control of individual gas loads and the timing of their injection, can be selected to control the shape of the gas puff and in particular to produce a quasispherical density profile if desired.

Valve 204 can be implemented, e.g., as an electrostatically actuated MEMS valve. Such implementations can operate at repetition rates up to 1 kHz or more. Implementations of nozzle 206 as e.g. a Laval nozzle can be fabricated by MEMS techniques on a silicon-on-insulator (SOI) wafer. Nozzles having any of various Mach numbers ranging from the subsonic to the supersonic are intended to fall within the scope of the invention. As mentioned above, Laval nozzles, among others, can be designed for Mach numbers up to 8, and possibly even up to 10 or more.

For x-ray generation, Mach numbers in the range of 0.5 to 10 are expected to be most preferable, with the higher Mach numbers in that range generally better than those at the low end of the range. The reason is that the higher Mach numbers will generally correspond to plasmas of lower density and lower stability, which conditions are expected to lead to more x-pinch-like behavior and a greater component of high-energy x-rays.

It should be noted in this regard that although x-ray generation is the most likely use for a device as described here, it may also have applications in which it is used to generate neutrons from fusion plasmas. Accordingly, our device should be broadly regarded as a device for radiation generation, with more specialized implementations being used for x-ray generation.

For x-ray generation, the injected gas is advantageously one or more of the noble gases, particularly xenon and krypton. For some applications, other gases, such as uranium hexafluoride, may also be useful. As those skilled in the art will understand, the energy of generated x-rays is readily tuned by selection of the gas to be injected.

The response time of the gas supply can be minimized by incorporating the valve 204 in a nozzle chip. According to an example, the valve 204 can be actuated in less than 50 μs with a 75 to 100 V actuation signal. Accordingly, in one scenario the valve 204 is opened and flow established prior to pulsed power source 114 firing an electrical pulse, exemplarily of 10-100 ns pulse width, to create the plasma pinch. Valve 204 is then closed, and a vacuum pump purges chamber 108.

Figure 3:
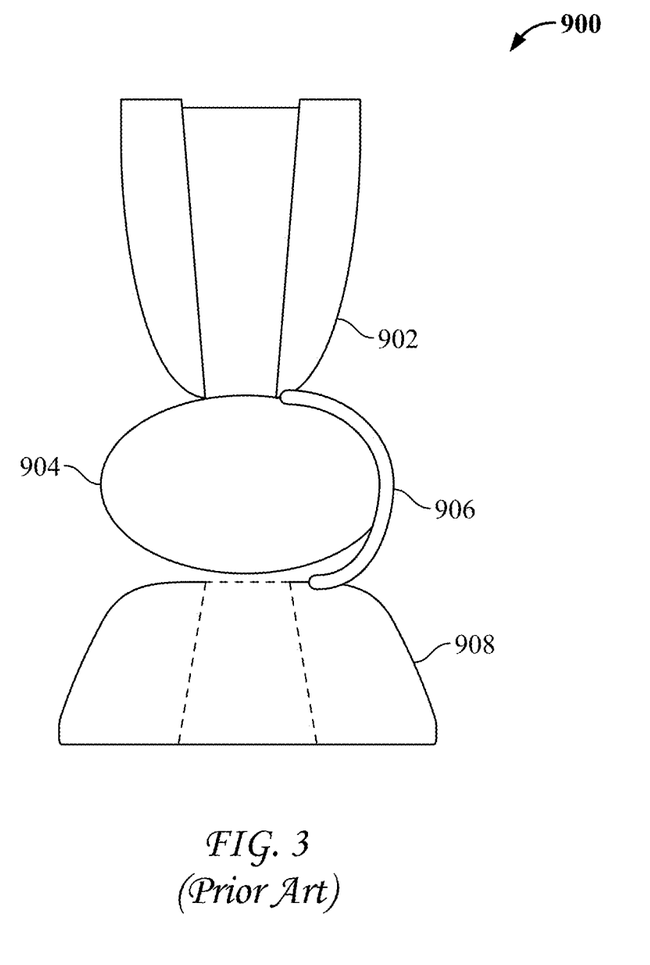
FIG. 3 illustrates a schematic diagram of another exemplary micro fluid-puff based source that includes a micro-scale fluid supply that injects a puff of fluid between an anode and a cathode within a chamber as known in the prior art.

FIG. 3 provides, in partially schematic wise, a cross-sectional view of a micropuff source 900 in which microscale fluid supply 902 includes a subsonic nozzle that injects gas puff 904 between the anode (not shown as a separate element) and cathode 908. Also shown in the figure is the current sheath 906 that forms upon electrical discharge. A current return structure, which may e.g. consist of a grounded conducting sheath surrounding the micropuff source, is typically included but is not shown in the figure.

A typical Mach number for the gas puff in this arrangement is 0.5. Gas injection at such a low Mach number can lead to formation of a puff that exhibits a quasispherical density profile.

Spectral studies of the emission from compressed plasmas have provided evidence of a high-energy tail in which the spectral radiance is significantly greater than that predicted by the blackbody radiation curve. According to our current belief, this phenomenon is attributable to the acceleration of electrons in the plasma by a structure, driven by the Raleigh-Taylor instability, that consists of regions of relatively high electric field and low pressure, in alternation with regions of low field and high pressure.

For at least some applications, the enhanced spectral radiance at high energy is desirable because, among other things, it makes parts of the x-ray spectrum accessible, for a given input voltage, that would not be accessible in a system characterized by equilibrium emission. Hence there may be applications for which it is advantageous to excite the plasma with disturbances that are designed to feed the Raleigh-Taylor instability.

To provide one such disturbance, a pulsed electron beam is generated using a tungsten emitter tip or sharp edge microfabricated, e.g., as part of the cathode, and an accelerating screen placed between the cathode and the anode.

Another type of disturbance that may be useful for feeding the Rayleigh-Taylor instability is resonant optical excitation provided by a laser such as a vertical cavity surface-emitting laser (VCSEL). For example, light at a resonant frequency of the plasma instability may be directed from a VCSEL external to the catheter to the reaction chamber by an optical fiber threaded through the catheter.

Figure 4:
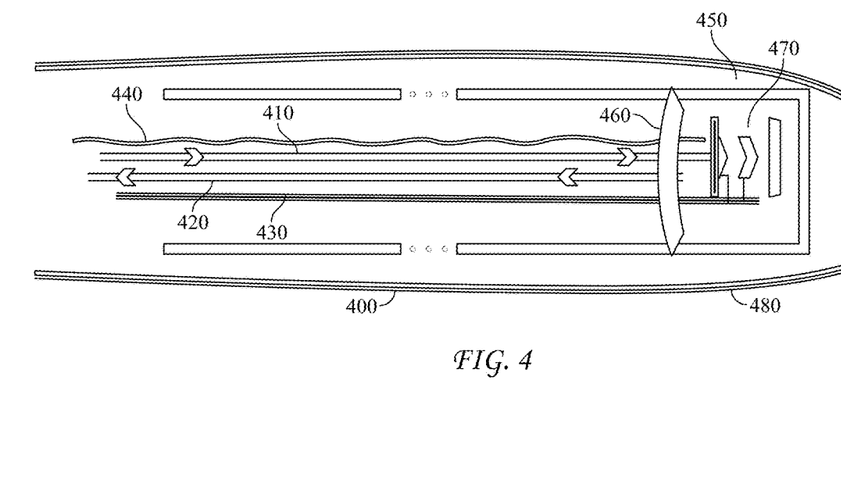
FIG. 4 provides a schematic, cross-sectional view of a catheter 400 that has been equipped with a source of medical x-rays according to an embodiment of the present invention.

FIG. 4 provides a schematic, cross-sectional view of a catheter 400 that has been equipped with a source of medical x-rays according to an embodiment of the present invention. As seen in the figure, the catheterized system includes capillary fill tube 410, capillary exhaust tube 420, transmission line 430, optical fiber 440, reaction chamber 450 with vacuum seal 460, and micropuff source 470. We believe that the reaction chamber, including the micropuff source, can be made to fit within an envelope several millimeters in maximum extent.

Although element 460 is described, above, as a "vacuum seal," it should be understood that in some of the contemplated implementations, the reaction chamber may be filled to an overpressure with a plasma-forming gas. In such implementations, element 460 is a pressure seal. In other implementations, the reaction chamber may simply be filled at atmospheric pressure, in which cases the seal is merely an isolation seal.

As mentioned above, the optical fiber is for the optional purpose of supplying light at a resonant wavelength for driving a Rayleigh-Taylor instability in the plasma. We believe that for applications in which only a limited number of pulses are required, the fill and exhaust tubes may also be optional. That is, we believe that a sealed reaction chamber may be satisfactory in a disposable unit intended for a single treatment requiring only a few pulses of x-radiation. Of course in a sealed implementation, the valve is not needed and the anode may wholly or partly occupy the space otherwise occupied by the nozzle.

With further reference to FIG. 4, it will be seen that the catheterized system includes an outer skin 480, which advantageously includes on the inside a flexible metallic sheath to serve as an electromagnetic shield, and on the outside an insulative, biocompatible polymeric layer. The total diameter of the package enclosed within skin 480 can be made as low as 5 mm initially, and in time we anticipate it can be made 2 mm or less.

An exemplary transmission line is designed to support a voltage pulse in the range 1-50 kV, or more particularly the range 5-10 kV, with a pulse width in the range 50-1000 ns, or more particularly about 100 ns, and a peak current in the range 1-50 amperes, or more particularly about 5 amperes. We believe that an appropriate cable containing such a transmission line can be made with an outer diameter of a few millimeters, which would be small enough to fit within a medical catheter. For some applications, it may be advantageous to combine the functions of transmission line and fill tube by introducing gas to the reaction chamber through a capillary bore that extends through the center of the central conductor of the transmission line. In such an arrangement, the central conductor would terminate concentrically on a valve-and-nozzle assembly.

If separate capillary tubes are to be used for gas fill and exhaust, one suitable choice would be glass tubes having, e.g., a 100 μm internal diameter. Both larger and smaller tubes are commercially available.

Typical gas pressures will be in the range 1-10 atm, but in implementations may be as low as 0.01 atm or less, and in other implementations may be as high as 100 atm or even somewhat more.

The nozzle and electrodes are advantageously made from silicon or related materials, such as silicon carbide, using known techniques of silicon microfabrication. Under high thermal loading conditions, however, it may for some applications be more desirable to make the nozzle and electrodes from tungsten or other refractory electrically conductive materials.

A cable for transmitting the signal needed to operate the valve is not shown in the figure. Diagnostics devices and their cables may optionally also be included within the catheter, but for simplicity are omitted from the figure.

Figure 5:
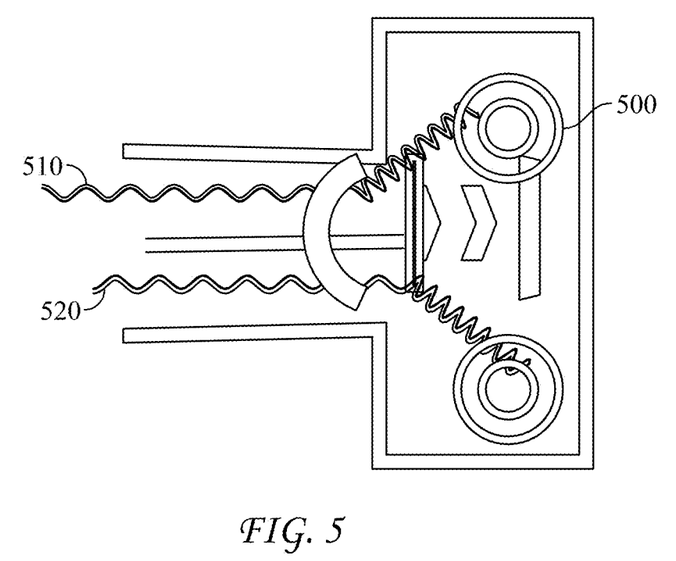
FIG. 5 shows a simplified detail of FIG. 4, including a cooling ring.

Active cooling of the reaction chamber may be desirable in some cases, particularly for applications in which loss of x-ray generation efficiency due to heating would be unacceptable. FIG. 5 shows a simplified detail of FIG. 4, in which cooling ring 500 is fed by coolant tubes 510 and 520, which are inserted through the catheter and which circulate a suitable gaseous or liquid coolant.

It will be understood from the preceding discussion that in our exemplary implementations, the nozzle is either coextensive with an electrode, exemplarily the anode, or is concentric with the anode and either surrounded by it or offset from it in the axial direction. In particular, therefore, it will be understood that in such examples, the gas jet is principally directed in an axial direction toward the cathode. The, e.g., cathode is typically of an annular conformation having a central hole. A portion of the positive ions that are generated in the plasma discharge and accelerated toward the cathode will pass through the central hole and may be collected on a separate stop plate, or "beam dump", which in at least some implementations may also be useful as a heat sink.

For the dissipation of mechanical shock induced by the electric discharges, it will be useful to employ, within the catheter, a combination of ductile and brittle materials in at least partial alternation. Appropriate choices of material, both for the elements already mentioned and also as additional packing and structural materials, will be known to those skilled in the art.

Those learned in the art of gaseous discharges will understand that plasmas are often characterized by their temperature and by a non-equilibrium temperature-correction factor represented by the Greek letter κ ("kappa"). This parameter is used to model the non-Maxwellian velocity distribution of high-energy electrons in the plasma. Our computational modeling studies have shown that the x-ray spectra of the plasma discharges produced by devices such as we describe here tend to become richer in high-energy x-rays as κ decreases. For example, when we modeled one representative fixed-energy plasma, we found, neglecting the x-ray line radiation, that the fraction of total x-radiation that exceeded 10 keV in energy was 6.8% at a κ value of 1.6, decreasing to only 0.0072% at a κ of 2, and decreasing still further to 0.00038% at a κ of 3.

For the x-rays generated by our device to be effective, they must be sufficiently penetrating to escape from the plasma reaction chamber and the catheter. As a general rule, we therefore believe that the useful part of the x-ray spectrum will be approximately the portion above 10 keV in energy.

Hence, it will be desirable according to our calculations to generate plasmas for which κ is approximately 1.6 or less. To generate such plasmas, the device parameters should, as a general rule, be set to provide a high-density plasma, and in particular a high-density plasma region slightly displaced from a region of high electromagnetic field. The injection of a dense fluid such as liquefied xenon may be useful in this regard, as may be the use of an annular nozzle, because the annular geometry tends to make the plasma more unstable. A relatively long pulse width may also be useful to afford more time for instability growth.

The treatment of tumors is one exemplary application for our device. The total x-ray energy dose deposited in the target tissue per exposure may, for example, fall within an order of magnitude of 0.025 Joule. The total dose may be contained within a single pulse, or it may be cumulative over a sequence of pulses. For such a purpose, the transmission line might deliver, for example, 0.1 Joule of electrical energy in a pulse 100 ns long at 10 kV and 100 amperes. A train of ten such pulses would therefore deliver a total of 1 Joule to the reaction chamber.

We have estimated that the efficiency of converting electrical energy to x-rays of energies exceeding 10 keV in the emission from a plasma of 1 keV temperature and κ of 1.6 is 0.35% to 1.4%. Hence to deliver a deposited dose of 0.025 Joule would call for a train of 18-90 pulses of the type described above.

Radiological imaging is another exemplary application for our device. To form an x-ray image, the device would be placed within the subject's body, and an imaging detector or detector array would be placed externally or, under special circumstances, at an appropriate position within the subject's body. X-ray doses for imaging are typically three orders of magnitude smaller than those required for tumor treatment. Hence an exemplary imaging exposure might be generated by a single electrical pulse 100 ns long at 10 keV and 10 ampere.

Figure 6:
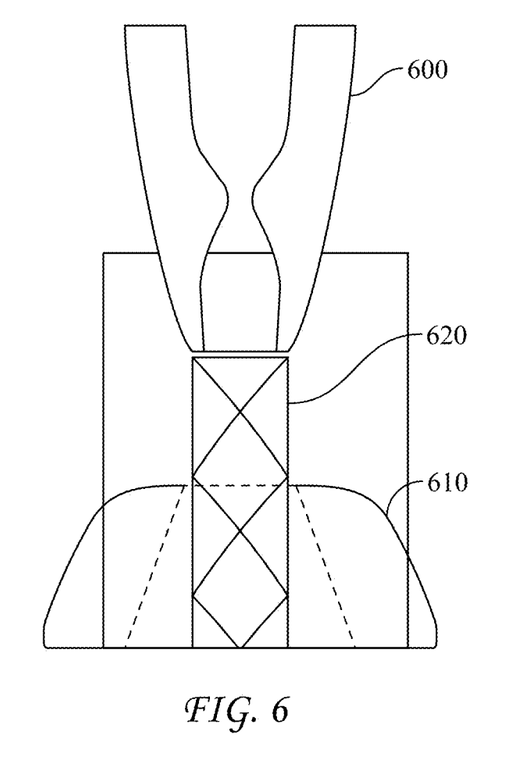
FIG. 6 provides a cross-sectional view of an assembly consisting of a Laval nozzle and an annular cathode according to an embodiment of the invention.

FIG. 6 provides a cross-sectional view of an assembly consisting of a Laval nozzle 600 and an annular cathode 610. A jet 620 of injected gas is also shown in the figure. The type of nozzle shown in the figure can be fabricated using known MEMS techniques.

Figure 7A:
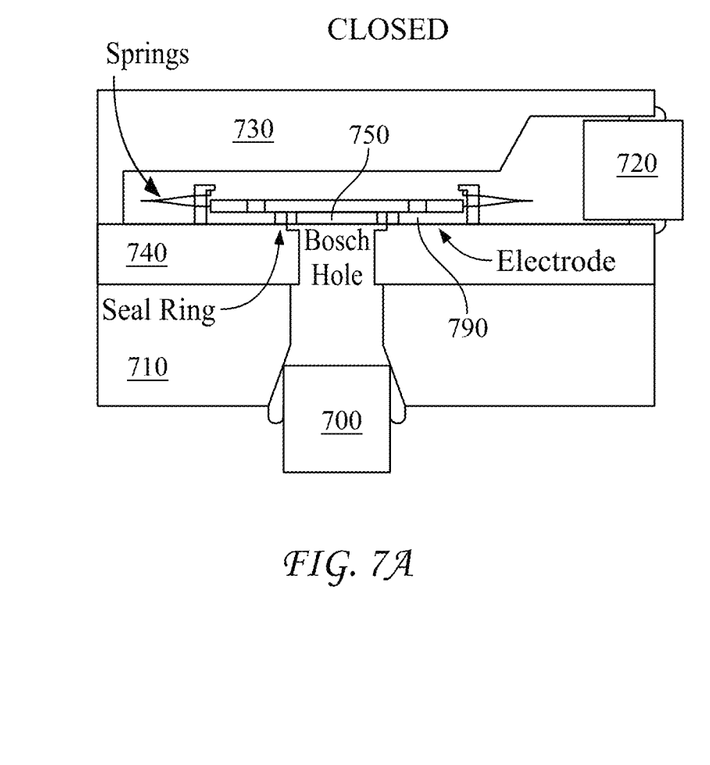
FIGS. 7A and 7B provide cross-sectional side views, in respectively the closed and open states, of a MEMS valve, which is one example of a valve that would be useful in the present context.
Figure 7B:
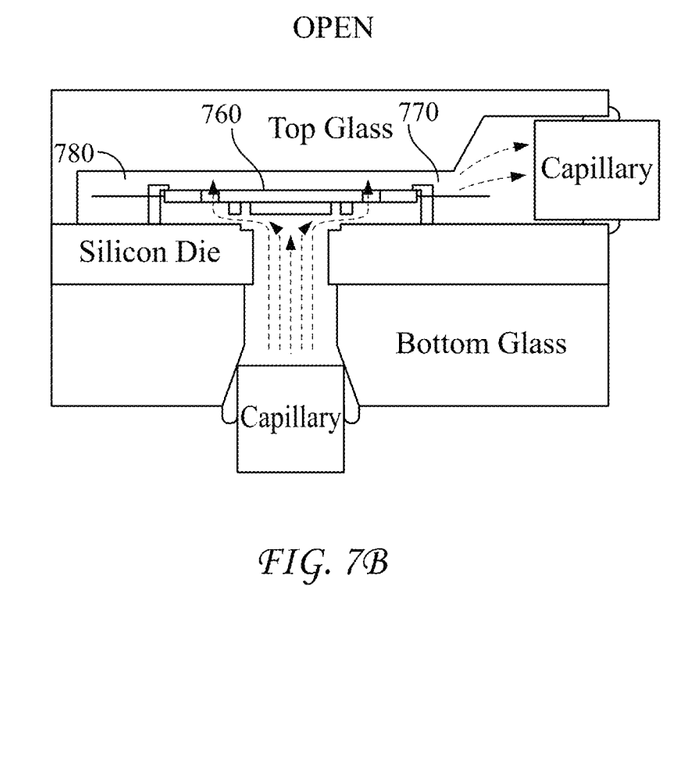

FIGS. 7A and 7B provide cross-sectional side views, in respectively the closed and open states, of a MEMS valve, which is one example of a valve that would be useful in the present context. As seen the figure, the valve is used to controllably open and close a path that connects capillary 700, the end of which is seated in a capture cone Bosch etched in lower glass plate 710, to capillary 720, the end of which is seated in a capture cone Bosch etched in upper glass plate 730. The valve mechanism is formed, using silicon microfabrication techniques, on valve die 740. As seen in the figure, the path is closed, when the valve is activated, by plug 750, which is a portion of floating member 760, which is suspended by springs 770 from anchors 780.

Activation is by electrostatic attraction between the floating member and the underlying die substrate when electrodes 790 are suitably energized.

A valve similar to that depicted in FIGS. 7A and 7B is described in P. Galambos et al., "Active MEMS Valves for Flow Control in a High-Pressure Micro-Gas-Analyzer," J. Microelectromechanical Syst. 20 (October 2011) 1150-1162, which was cited above.

Another application for our device is for flash radiography in which, for example, the catheter is positioned near a moving mechanical object and a burst of x-rays is generated for collection by an imaging detector or imaging detector array after transmission through or scattering by the object. It is noteworthy in this regard that, according to our present belief, pulses ranging in length from several milliseconds down to a nanosecond or less will be achievable by the techniques described here.

Yet another application is for phase-contrast imaging. In one possible approach to phase-contrast imaging, the device is pulsed multiple times while incrementally shifting in position along a scan pattern between pulses. Resulting differences in the radiation intercepted by the detector or detector array are processed and interpreted as image information.

What is claimed is:

1. An x-ray-generating apparatus, comprising: a catheter; a plasma discharge chamber situated within a terminal portion of the catheter; a cathode and an anode positioned within the plasma discharge chamber and separated by a gap; and a high-voltage transmission line extensive through the interior of the catheter and terminating on the cathode and anode so as to deliver, in operation, one or more voltage pulses across the gap;

wherein the x-ray-generating apparatus comprises a nozzle situated within the plasma discharge chamber, and wherein the nozzle is conformed to inject a flow of plasma-forming fluid into the gap at a velocity in the range Mach 0.5 to Mach 10.

2. The apparatus of claim 1, further comprising a fill tube extensive through the interior of the catheter and terminating at the plasma discharge chamber so as to deliver, in operation, a flow of plasma-forming fluid to the plasma discharge chamber; and an exhaust tube extensive through the interior of the catheter and terminating at the plasma discharge chamber so as to permit the removal of gas from the plasma discharge chamber.

3. The apparatus of claim 1, further comprising an inlet tube and an outlet tube for circulating a coolant within the catheter.

4. The apparatus of claim 1, wherein the nozzle is coextensive with the cathode or the anode.

5. The apparatus of claim 1, further comprising a valve situated within the catheter, coupled to a fill tube so as to receive in-flowing plasma-forming fluid therefrom, and coupled to the nozzle so as to controllably discharge the in-flowing plasma-forming fluid thereinto.

6. The apparatus of claim 5, wherein the valve is a silicon microfabricated valve.

* * * * *